(12) United States Patent
Nezuka (10) Patent No.: US 9,182,433 B2
(45) Date of Patent: *Nov. 10, 2015

(54) DETECTION CIRCUIT FOR CAPACITIVE SENSOR

(71) Applicant: DENSO CORPORATION, Kariya, Aichi-pref (JP)

(72) Inventor: Tomohiro Nezuka, Kariya (JP)

(73) Assignee: DENSO CORPORATION, Kariya (JP)

( * ) Notice: Subject to any disclaimer, the term of this patent is extended or adjusted under 35 U.S.C. 154(b) by 116 days.

This patent is subject to a terminal disclaimer.

(21) Appl. No.: 13/936,250

(22) Filed: Jul. 8, 2013

(65) Prior Publication Data

US 2014/0015550 A1  Jan. 16, 2014

(30) Foreign Application Priority Data

Jul. 13, 2012 (JP) .................................. 2012-157524

(51) Int. Cl.
*G01R 27/26* (2006.01)
*G01N 27/22* (2006.01)

(52) U.S. Cl.
CPC .......... *G01R 27/2605* (2013.01); *G01N 27/228* (2013.01)

(58) Field of Classification Search
CPC .......... G01R 27/2605; G01R 19/0084; G01R 17/00; G01R 17/02
USPC ........................... 324/679, 658, 647, 665, 674
See application file for complete search history.

(56) References Cited

U.S. PATENT DOCUMENTS

| | | | |
|---|---|---|---|
| 2002/0175692 A1* | 11/2002 | Lasalandra et al. | 324/684 |
| 2003/0052699 A1* | 3/2003 | Lasalandra et al. | 324/662 |
| 2007/0163815 A1* | 7/2007 | Ungaretti et al. | 178/18.06 |
| 2008/0022762 A1 | 1/2008 | Skurnik | |
| 2010/0007428 A1* | 1/2010 | Nezuka | 331/36 C |
| 2012/0326905 A1* | 12/2012 | Nezuka | 341/136 |
| 2014/0015544 A1* | 1/2014 | Nezuka | 324/603 |

FOREIGN PATENT DOCUMENTS

| | | | | |
|---|---|---|---|---|
| JP | 2008-102091 | * | 5/2008 | ................ G01L 9/00 |
| JP | 2008-102091 A | | 5/2008 | |

OTHER PUBLICATIONS

Office Action mailed May 13, 2014 issued in corresponding JP patent application No. 2012-157524 (and English translation).

(Continued)

*Primary Examiner* — Tung X Nguyen
*Assistant Examiner* — Alesa Allgood
(74) *Attorney, Agent, or Firm* — Posz Law Group, PLC (57) ABSTRACT

A detection circuit for a capacitive sensor includes a drive signal generator for applying drive signal varying between first and second levels to a sensor common terminal, a sense amplifier having input terminals respectively connected to sensor detection terminals, and a controller for controlling input common-mode voltage of the sense amplifier to predetermined voltage. The controller includes a feedback amplifier for outputting feedback voltage according to difference between the common-mode and predetermined voltages, a pair of feedback capacitors having one ends respectively connected to the detection terminals and another ends connected together, and a voltage switcher for applying preset voltage, between the predetermined voltage and a limit voltage outputtable by the feedback amplifier in direction where the second level exists relative to the first level, to the other ends during the first level and the feedback voltage to the other ends during the second level.

6 Claims, 5 Drawing Sheets

(56) References Cited

OTHER PUBLICATIONS

Lemkin, Mark and Bernhard E. Boser. "A Three-Axis Micromachined Accelerometer with a CMOS Position-Sense Interface and Digital Offset-Trim Electronics," IEEE Journal of Solid-State Circuits, 34(4), 456-468, Apr. 1999. (Discussed on pp. 1-2 of the specification.).

U.S. Appl. No. 13/936,256, filed Jul. 8, 2013, Nezuka.

* cited by examiner

FIG. 1A
Reset

DETECTION CIRCUIT FOR CAPACITIVE SENSOR

CROSS REFERENCE TO RELATED APPLICATION

This application is based on Japanese Patent Application No. 2012-157524 filed on Jul. 13, 2012, the contents of which are incorporated herein by reference.

FIELD

The present disclosure relates to a detection circuit having a common-mode feedback circuit and used for a capacitive sensor.

BACKGROUND

A capacitive sensor has a pair of sense capacitors with capacitances, the difference between which changes according to a physical quantity such as acceleration or pressure. One ends of the sense capacitors are connected together to provide a common terminal. Another ends of the sense capacitors are configured to provide separate detection terminals. The detection circuit applies a drive signal varying between two levels to the common terminal, converts the difference between the capacitances of the sense capacitors to a voltage, and outputs an electrical signal having a voltage value according to the physical quantity.

A detection circuit with a fully differential switched capacitor amplifier (sense amplifier) has been proposed as an example of this type of detection circuit (refer to a non-patent document 1). This detection circuit has a great effect on suppression of common-mode noise, is capable of reducing errors such as charge injection and clock feedthrough, and is capable of increasing amplitude of an output signal by using differential output.

Even when a fully differential amplifier is simply used in a detection circuit, a voltage at an input terminal varies largely according to a drive signal. A sense amplifier needs to have a wide input range for a variation in an input common-mode voltage. Further, influence of a mismatch of a parasitic capacitance at an input terminal of a C-V conversion circuit appears, and influence of an offset of a sense amplifier depending on an input common-mode voltage appears. Therefore, in the detection circuit disclosed in the non-patent document 1, a common-mode feedback loop is added to stabilize an input common-mode voltage to a desired constant voltage.

In another configuration to stabilize an input common-mode voltage, one end of a compensation capacitor is connected to a detection terminal, and an inversion signal opposite in phase to a drive signal is applied to the other end (refer to a patent document 1). In practice, even in this configuration, a common-mode feedback loop is necessary to prepare for a difference in capacitance between a sense capacitor and a compensation capacitor due to, for example, manufacturing variation, aging degradation, and temperature drift.

PRIOR ART DOCUMENT

Patent Document

[Patent Document 1] US 2007/0163815A

Non-Patent Document

[Non-Patent Document 1] "A Three-Axis Micromachined Accelerometer with a CMOS Position-Sense Interface and Digital Offset-Trim Electronics" by M. Lemkin, B. E. Boser, IEEE Journal of Solid-State Circuits, Vol. 34, No. 4, April 1999, pp. 456-468

SUMMARY

In the detection circuit disclosed in the non-patent document 1, a feedback capacitor having a sufficiently large capacitance relative to a sense capacitor is necessary. Even in the detection circuit disclosed in the patent-document 1, because of the wide capacitance range of the sense capacitor, the capacitance of the feedback capacitor needs to be large to allow wide variations in capacitances of the sense capacitor and the compensation capacitor. If the capacitance of the feedback capacitor is small, an output of the feedback capacitor varies according to the difference in capacitance between the sense capacitor and the compensation capacitor, and the input common-mode voltage deviates due to the fact that the gain of the feedback amplifier is finite.

However, as described in the patent document 1, when the capacitances of the capacitors (sense capacitor, compensation capacitor) connected to the input terminal of the sense amplifier are increased, noise charge amount is increased. As a result, the accuracy of the C-V conversion performed by the detection circuit may be degraded. That is, in the conventional structures, since the amount of deviation of the input common-mode voltage from a desired value has a conflicting relationship with the amount of noise, the detection accuracy is degraded in either case.

In view of the above, it is an object of the present disclosure to provide a detection circuit used for a capacitive sensor and configured to achieve high detection accuracy with a common-mode feedback circuit.

According to an aspect of the present disclosure, a detection circuit is used for a capacitive sensor including a pair of sense capacitors with capacitances having a difference responsive to a physical quantity. One ends of the sense capacitors are connected together to provide a common terminal, and another ends of the sense capacitors are configured to provide separate detection terminals. The detection circuit includes a drive signal generation circuit capable of generating and applying a drive signal varying between a first level and a second level to the common terminal, a fully differential sense amplifier having inverting and non-inverting input terminals respectively connected to the detection terminals and being capable of outputting a differential voltage according to the difference between the capacitances of the sense capacitors, and a common-mode voltage control circuit capable of controlling an input common-mode voltage of the sense amplifier to a predetermined voltage.

The common-mode voltage control circuit includes a feedback amplifier, a pair of feedback capacitors, and a voltage switch circuit. The feedback amplifier outputs a feedback voltage according to a difference between the input common-mode voltage and the predetermined voltage. The feedback capacitors have one ends respectively connected to the detection terminals and have another ends connected together. The voltage switch circuit applies a preset voltage to the other ends of the feedback capacitors to charge the feedback capacitors during the first level of the drive signal and applies the feedback voltage instead of the preset voltage to the other ends of the feedback capacitors during the second level of the drive signal. The preset voltage has a voltage value between the predetermined voltage and a limit voltage outputtable by the feedback amplifier in a voltage direction in which the second level exists relative to the first level.

BRIEF DESCRIPTION OF THE DRAWINGS

The above and other objects, features, and advantages will become more apparent from the following description and drawings. In the drawings.

DETAILED DESCRIPTION

In each embodiment, the same symbols will be used to represent substantially the same portions to omit explanation. Since each embodiment relates to control of an input common-mode voltage, a structure unrelated to the control is omitted.

First Embodiment

Figure 1A:
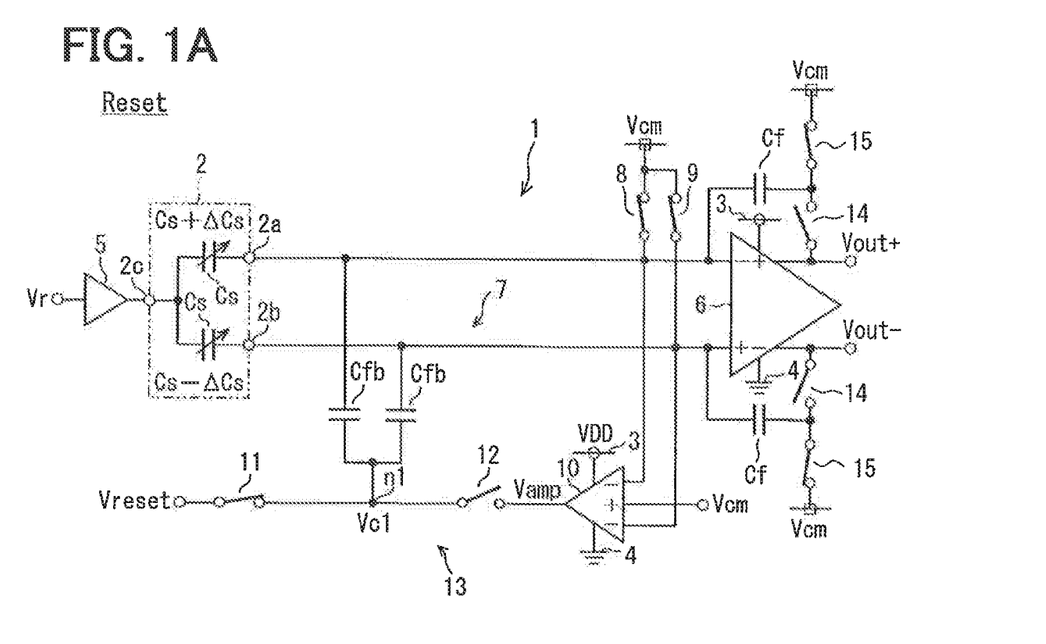
FIG. 1A is a diagram illustrating a detection circuit during a period Reset according to a first embodiment of the present disclosure.
Figure 1B:
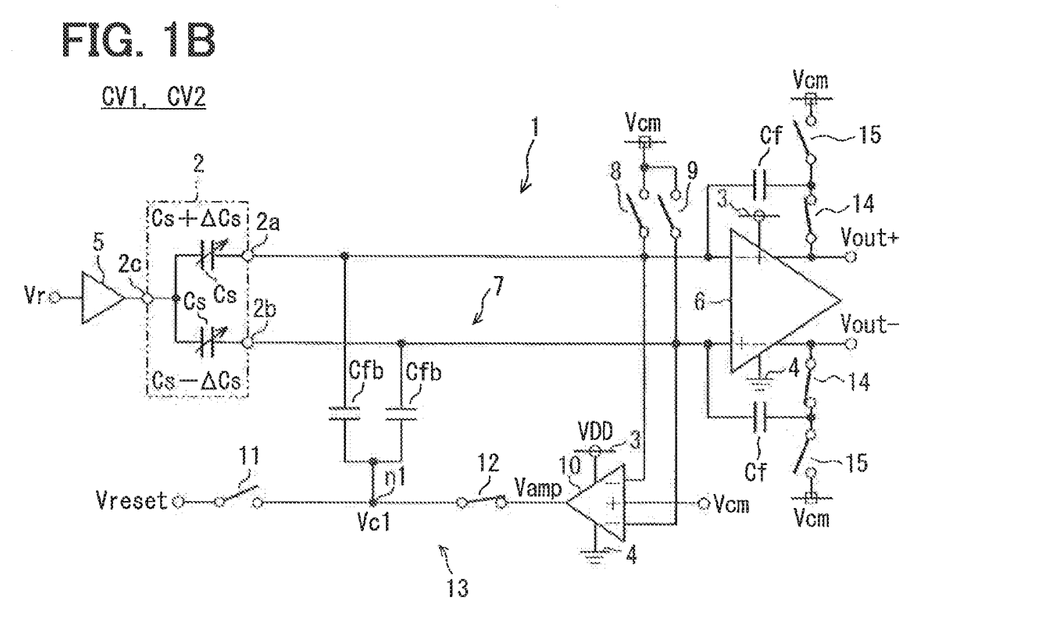
FIG. 1B is a diagram illustrating the detection circuit during a period CV1 and a period CV2 according to the first embodiment of the present disclosure.
Figure 2:
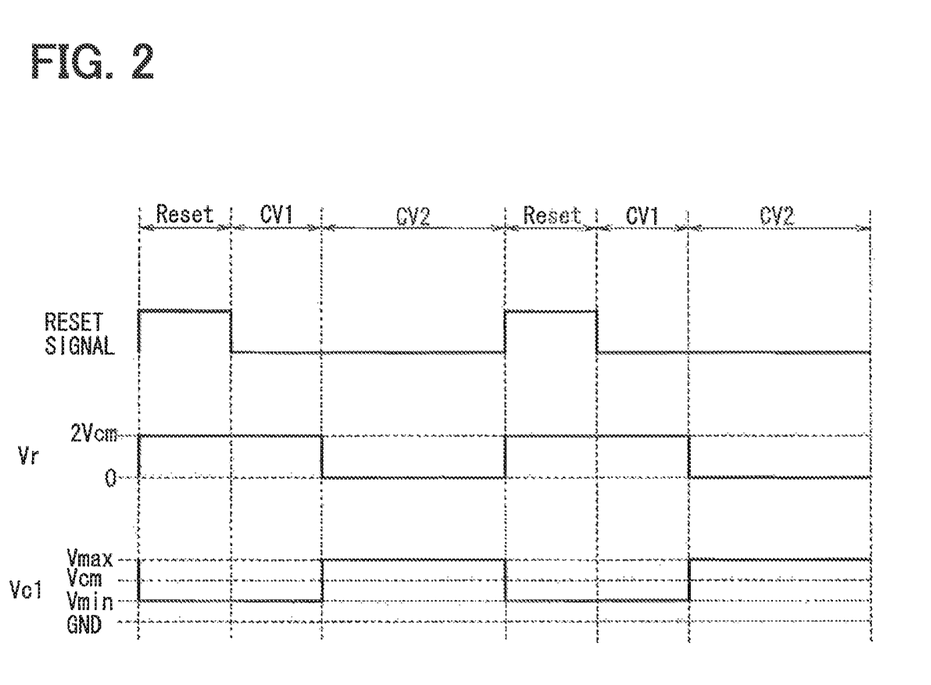
FIG. 2 is a waveform diagram illustrating control of an input common-mode voltage according to the first embodiment of the present disclosure.

A first embodiment is described below with reference to FIG. 1A, FIG. 1B, and FIG. 2. A fully differential detection circuit 1 shown in FIG. 1A and FIG. 1B performs a C-V conversion for a capacitive sensor 2 and outputs a detection signal indicative of a physical quantity such as acceleration or pressure. A CDS (correlated double sampling) circuit, which is not shown in the drawings, is connected to a latter part of the detection circuit 1 in order to eliminate an influence of an offset voltage of an operational amplifier from the detection signal. The detection circuit 1 operates on a power supply voltage VDD supplied through power supply lines 3 and 4.

The capacitive sensor 2 includes a pair of sense capacitors Cs with capacitances changing in opposite phase according to the physical quantity in such a manner that when one sense capacitor Cs has the capacitance of Cs+ΔCs, the other sense capacitor Cs has the capacitance of Cs−ΔCs. One ends of the sense capacitors Cs are connected together to provide a common terminal 2c. The other ends of the sense capacitors Cs provide separate detection terminals 2a and 2c. The detection circuit 1 includes a drive signal generation circuit 5 and applies a drive signal Vr varying between a first level (e.g., twice a predetermined voltage Vcm) and a second level (e.g., 0V) to the common terminal 2c.

The detection circuit 1 includes a fully differential sense amplifier 6 with an inverting input terminal connected to the detection terminal 2a and a non-inverting input terminal connected to the detection terminal 2b. The sense amplifier 6 outputs a differential voltage according to a difference ±ΔCs between the capacitances of the sense capacitors Cs. A capacitor Cf with a capacitance of Cf is connected between the input and output terminals of the sense amplifier 6. The detection circuit 1 includes a common voltage control circuit 7 for controlling an input common-mode voltage of the sense amplifier 6 so that the input common-mode voltage can be equal to a predetermined voltage Vcm.

The predetermined voltage Vcm is set close to a median value between the power supply voltage VDD and a ground voltage 0V. A reason for this is that the median value is suitable for preventing a level of the input terminal from exceeding the power supply voltage when the level transiently varies due to drive of the sense capacitor Cs and also suitable for an operational amplifier to generate the median value when the predetermined voltage Vcm is generated by using the operational amplifier. Switches 8 and 9 for application of the predetermined voltage Vcm are connected to the respective input terminals of the sense amplifier 6. A switch 14 for connection to an output terminal of the sense amplifier 6 and a switch 15 for application of the predetermined voltage Vcm are connected to an output-side terminal of each capacitor Cf. A common-mode voltage control circuit for controlling an output common-mode voltage so that the output common-mode voltage can be equal to the predetermined voltage Vcm is incorporated in the sense amplifier 6.

The common-mode voltage control circuit 7 includes a feedback amplifier 10, a pair of feedback capacitors Cfb, and a voltage switch circuit 13 constructed with switches 11 and 12. The feedback amplifier 10 is configured as a switched-capacitor circuit and outputs a feedback voltage Vamp (=gain×(predetermined voltage Vcm−input common-mode voltage)+constant voltage Vc) by amplifying a difference between the predetermined voltage Vcm and the input common-mode voltage which is an average voltage of two inverting input terminals. In the description below, the constant voltage Vc is assumed to be equal to the predetermined voltage Vcm, but not limited to it.

One ends of the feedback capacitors Cfb are connected to the respective detection terminals 2a and 2b. The other ends of the feedback capacitors Cfb are connected together to a node n1. A preset voltage Vreset is applied to the node n1 through the switch 11, or the feedback voltage Vamp is applied to the node n1 through the switch 12. The switches 8, 9, 11, and 15 are ON during a time period where a Reset signal is at a H level, and the switches 12 and 14 are ON during a time period where a Reset signal is at a L level.

Next, an effect associated with the control of the input common-mode voltage of the sense amplifier 6 is described. As shown in FIG. 2, the input common-mode voltage is controlled by repeating (a) a period Reset, (b) a period CV1, and (c) a period CV2 in turn. The drive signal Vr becomes 2Vcm (first level) during the period Reset and the period CV1 and becomes 0V (second level) during the period CV2. Vc1 represents a voltage at the node n1. In calculations described below, unless otherwise noted, the gain of the feedback amplifier is assumed to be infinity.

During the period Reset, the switches 12 and 14 are OFF, and the switches 8, 9, 11, and 15 are ON. Thus, the preset voltage Vreset is applied to the node n1 so that charge can be stored in the feedback capacitors Cfb to counter the inversion of the level of the drive signal Vr. The preset voltage Vreset is a voltage existing in a voltage direction in which the second level exists relative to the first level with respect to the predetermined voltage Vcm, i.e., is a voltage existing in a low voltage direction with respect to the predetermined voltage Vcm.

Then, during the period CV1, the switches 8, 9, 11, and 15 are OFF, and the switches 12 and 14 are ON, so that a common-mode feedback loop can be formed through the feedback capacitors Cfb. At this time, the feedback amplifier 10 needs to have a gain enough to achieve a feedback control effect so that input common-mode voltage can be equal to the predetermined voltage Vcm. Therefore, the present voltage Vreset is set to a voltage value between a lower limit voltage Vmin, which is outputtable by the feedback amplifier 10 with a sufficient gain, and the predetermined voltage Vcm.

As described later, it is preferable that the preset voltage Vreset be set to a lower value to reduce the capacitance of the feedback capacitor Cfb. However, if the preset voltage Vreset is set equal to the lower limit voltage Vmin, the sufficient gain may not be obtained due to a variation in gain characteristics of the feedback amplifier 10. For this reason, in practice, the preset voltage Vreset is set greater than the lower limit voltage Vmin by a margin corresponding to the gain variation.

During the period CV1, the sense amplifier 6 outputs a voltage which is the sum of the predetermined voltage Vcm and offset voltages of the sense amplifier and the feedback amplifier 10. The CDS circuit holds output voltages Vout+ and Vout− at this time.

During the period CV2, the switches are kept in the same condition as during the period CV1 so that the common-mode feedback loop can remain. When the drive signal Vr decreases from 2Vcm to 0V, the feedback voltage Vamp increases so that the input common-mode voltage can be equal to the predetermined voltage Vcm. At this time, the feedback voltage Vamp is a voltage existing in a voltage direction in which the first level exists relative to the second level with respect to the predetermined voltage Vcm, i.e., is a voltage existing in a high voltage direction with respect to the predetermined voltage Vcm.

At this time, since the feedback capacitor Cfb has the charge stored during the period Reset, the increase in the feedback voltage Vamp is reduced by the charge. In other words, the capacitance of the feedback capacitor Cfb necessary to keep the input common-mode voltage at the predetermined voltage Vcm can be reduced by the charge prestored in the feedback capacitor Cfb.

When calculated with respect to the input terminal of the sense amplifier 6, a common-mode charge QCV1 during the period CV1 can be given by an equation (1).

$$QCV1 = Cfb(Vcm - Vreset) - CsVcm \quad (1)$$

A common-mode charge QCV2 during the period CV2 can be given by an equation (2).

$$QCV2 = Cfb(Vcm - Vamp) + CsVcm \quad (2)$$

Since QCV1=QCV2 according to the law of conservation of charge, an equation (3) can be obtained.

$$Vamp = Vreset + (2Cs/Cfb)Vcm \quad (3)$$

The equation (3) indicates that the feedback voltage Vamp needs to be higher during the period CV2 as the capacitance of the sense capacitor Cs is larger or as the capacitance of the feedback capacitor Cfb is smaller. When the output voltage Vamp exceeds an upper limit voltage Vmax, the feedback amplifier 10 cannot have the gain enough to achieve the feedback control effect. Therefore, the capacitance of the feedback capacitor Cfb is set so that the feedback voltage Vamp during the period CV2 can be a value between the upper limit voltage Vmax and the predetermined voltage Vcm, preferably, a value smaller than the upper limit voltage Vmax by a margin corresponding to the gain variation.

It is noted that since the gain of the feedback amplifier 10 is finite, a voltage error of (output voltage Vamp−constant voltage Vc)/gain(=(output voltage Vamp−predetermined voltage Vcm)/gain) remains at the input terminal. For this reason, it is preferable that the gain of the feedback amplifier 10 be high.

As described above, according to the present embodiment, the detection circuit 1 controls the input common-mode voltage by the effect of the active common-mode feedback loop so that the input common-mode voltage can be equal to the predetermined voltage Vcm. Assuming that there is no common-mode feedback, the parasitic capacitance of the input terminal of the sense amplifier 6 has a temperature dependence and a voltage dependence even when the inverting side and the non-inverting side have the same characteristics (e.g., a capacitance, a temperature characteristic, a voltage characteristic). As a result, the amount by which the capacitive sensor 2 is driven varies so that sensitivity can vary. Further, if there is a parasitic capacitance mismatch between the inverting side and the non-inverting side, the amount by which the charge changes differs between the input terminals so that an offset can occur. If the temperature dependence or the voltage dependence of the parasitic capacitance differs between the inverting side and the non-inverting side, the mismatch amount varies depending on conditions, and therefore the offset can vary. The detection circuit 1 can reduce errors due to the parasitic capacitance by the effect of the common-mode feedback.

Since the preset voltage Vreset is applied during the period Reset so that the feedback capacitor Cfb can be precharged, the increase in the feedback voltage Vamp during the period CV2 is reduced accordingly. Thus, the capacitance of the feedback capacitor Cfb can be made small. When the capacitance becomes small, noise produced when the detection circuit 1 performs the C-V conversion is reduced so that the physical quantity can be accurately detected.

Further, as the preset voltage Vreset is set smaller, the capacitance of the sense capacitor Cs of the capacitive sensor 2 can be increased while maintaining the capacitance of the feedback capacitor Cfb unchanged.

Further, an applicable capacitance range as the feedback capacitor Cfb becomes wider by setting the preset voltage Vreset to a smaller value. Therefore, even when the capacitance of the sense capacitor Cs or the feedback capacitor Cfb varies, the above effect and advantage can be obtained.

Since the feedback voltage Vamp changes from a low voltage region to a high voltage region across the predetermined voltage Vcm, a range over which the feedback amplifier 10 can output the voltage can be effectively used. Therefore, the feedback amplifier 10 can have a narrower output voltage range than conventional structure. Further, unlike conventional structure, a phase-reversing driver is not used during the period CV1 and the period CV2. Therefore, the feedback system is not directly affected by noise from the power supply lines 3 and 4.

The period CV1 is provided between the period Reset and the period CV2, and the offset voltages of the amplifiers 6 and 10 are outputted to the CDS circuit. Thus, the physical quantity can be detected based on the difference in the output voltage between during the period CV1 and during the period CV2 without being affected by the offset voltages of the amplifiers 6 and 10. Further, since the detection circuit 1 has a fully differential structure, the detection circuit 1 has a great effect on suppression of common-mode noise, is capable of reducing errors such as charge injection and clock feedthrough, and is capable of increasing amplitude of an output signal.

Second Embodiment

Figure 3A:
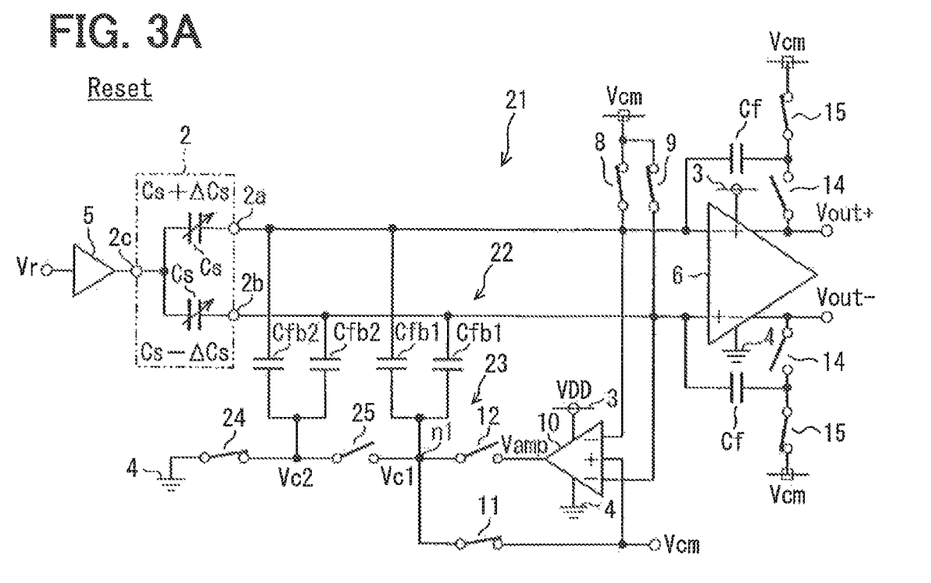
FIG. 3A is a diagram illustrating a detection circuit during a period Reset according to a second embodiment of the present disclosure.
Figure 3B:
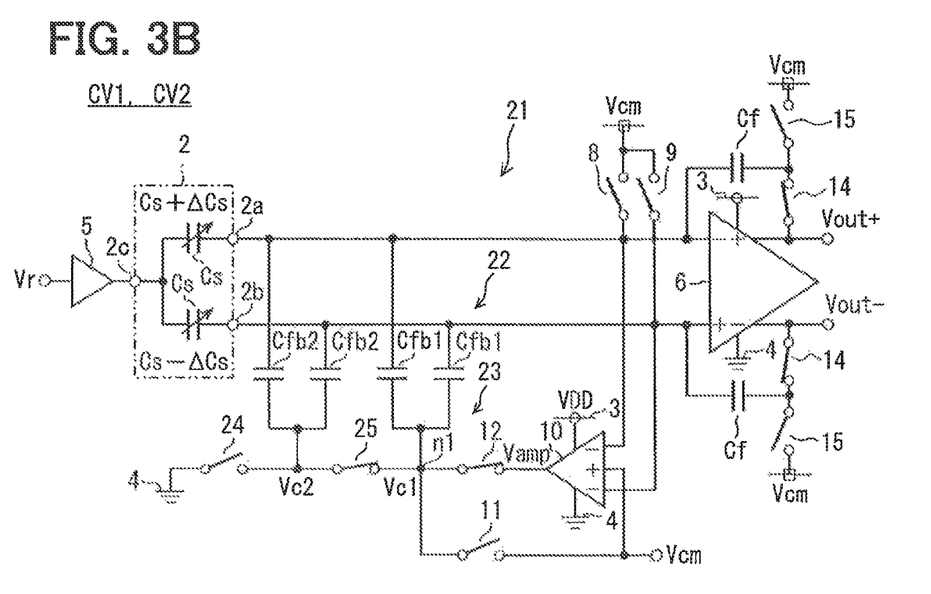
FIG. 3B is a diagram illustrating the detection circuit during a period CV1 and a period CV2 according to the second embodiment of the present disclosure.

Next, a second embodiment is described below with reference to FIGS. 3A, 3B, 4, 5A, and 5B. As shown in FIGS. 3A and 3B, a detection circuit 21 includes a common-mode voltage control circuit 22. The common-mode voltage control circuit 22 includes the feedback amplifier 10, a pair of first feedback capacitors Cfb1, a pair of second feedback capacitors Cfb2, and a voltage switch circuit 23 constructed with the switches 11 and 12 and switches 24 and 25. The first feedback capacitor Cfb1 and the second feedback capacitor Cfb2 correspond to a division of the feedback capacitor Cfb shown in FIGS. 1A and 1B by two.

One ends of the feedback capacitors Cfb1 are connected to the respective detection terminals 2a and 2b. The other ends of the feedback capacitors Cfb1 are connected together to the node n1. One ends of the feedback capacitors Cfb2 are also connected to the respective detection terminals 2a and 2b. The other ends of the feedback capacitors Cfb2 are connected together. The other ends of the feedback capacitors Cfb2 are connected to the power supply line 4 through the switch 24 and connected to the node n1 through the switch 25.

A voltage applied through the switch 24 is a voltage of the power supply line 4 on a voltage side where the second level (0V) exists relative to the first level (2Vcm) and corresponds to the second preset voltage. When the switch 25 is ON, the first feedback capacitor Cfb1 and the second feedback capacitor Cfb2 are connected in parallel to each other. The predetermined voltage Vcm corresponding to a first preset voltage is applied to the node n1 through the switch 11, or the feedback voltage Vamp is applied to the node n1 through the switch 12. The switches 8, 9, 11, 15, and 24 are ON during the time period where the Reset signal is at a H level, and the switches 12, 14, and 25 are ON during the time period where the Reset signal is at a L level.

Figure 4:
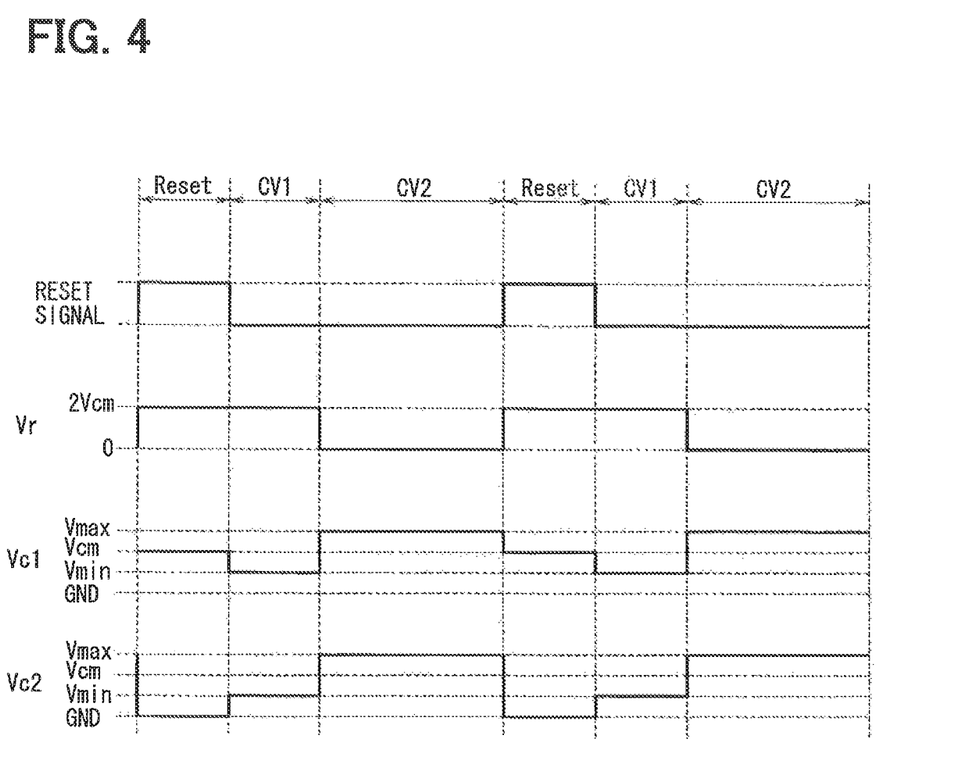
FIG. 4 is a waveform diagram illustrating control of an input common-mode voltage according to the second embodiment of the present disclosure.

Next, an effect according to the present embodiment is described. An explanation for the same effect as the first embodiment is omitted. Vc2 represents a voltage of the other end of the feedback capacitor Cfb2. As shown in FIG. 4, the common-mode voltage control circuit 22 repeats (a) a period Reset, (b) a period CV1, and (c) a period CV2 in turn.

During the period Reset, the switch 24 is ON, and the switch 25 is OFF, so that 0V can be applied to the other end of the feedback capacitor Cfb2. Thus, charge can be stored in the feedback capacitor Cfb2 to counter the inversion of the level of the drive signal Vr. Further, the switch 11 is ON so that the first preset voltage can be applied to the other end of the feedback capacitor Cfb1. According to the present embodiment, since the first present voltage is set equal to the predetermined voltage Vcm, no charge is stored in the feedback capacitor Cfb1.

During the period CV1 and the period CV2, the switch 24 is OFF, and the switch 25 is ON. Therefore, the feedback capacitors Cfb1 and Cfb2 are connected in parallel between the node n1 and the detection terminals 2a and 2b, so that a common-mode feedback loop can be formed through the parallel capacitors. When calculated with respect to the input terminal of the sense amplifier 6, a common-mode charge Qreset during the period Reset can be given by an equation (4).

$$Qreset = Cfb2 Vcm - Cs Vcm \quad (4)$$

A common-mode charge QCV1 during the period CV1 can be given by an equation (5).

$$QCV1 = (Cfb1 + Cfb2)(Vcm - Vamp) - Cs Vcm \quad (5)$$

Since Qreset=QCV1 according to the law of conservation of charge, an equation (6) can be obtained.

$$Vamp = (Cfb1/(Cfb1 + Cfb2)) Vcm \quad (6)$$

When the drive signal Vr decreases from 2Vcm to 0V after transition to the period CV2, the feedback voltage Vamp increase so that the input common-mode voltage can be equal to the predetermined voltage Vcm. A common-mode charge QCV2 during the period CV2 can be given by an equation (7).

$$QCV2 = (Cfb1 + Cfb2)(Vcm - Vamp) + Cs Vcm \quad (7)$$

Since QCV1=QCV2 according to the law of conservation of charge, an equation (8) can be obtained.

$$Vamp = ((Cfb1 + 2Cs)/(Cfb1 + Cfb2)) Vcm \quad (8)$$

This result is compared with a feedback voltage Vamp of a conventional structure having no feedback capacitor Cfb2. An equation (9) can be obtained by substituting zero for Cfb2, and it can be understood that Vamp of the present embodiment is lower than Vamp1 of the conventional structure (Vamp<Vamp1).

$$Vamp1 = ((Cfb1 + 2Cs)/Cfb1) Vcm \quad (9)$$

Further, an equation (10) can be obtained by substituting Cfb1+Cfb2 for Cfb1 in the equation (9) to compare the present embodiment with the conventional structure under a condition that the total capacitance of the feedback capacitor is equal to each other. Even under this condition, it can be understood that Vamp of the present embodiment is lower than Vamp2 of the conventional structure (Vamp<Vamp2).

$$Vamp2 = ((Cfb1 + Cfb2 + 2Cs)/(Cfb1 + Cfb2)) Vcm \quad (10)$$

A reason for this is that initial charge (=Cfb2Vcm) during the period Reset is canceled by charge which is transferred from the sense capacitor Cs due to a change in the drive signal Vr. Accordingly, the total capacitance Cfb1+Cfb2 can be reduced.

According to the present embodiment, the capacitances of the feedback capacitors Cfb1 and Cfb2 are set so that the feedback voltage Vamp during the period CV2 can be a value between the upper limit voltage Vmax and the predetermined voltage Vcm, preferably, a value smaller than the upper limit voltage Vmax by the margin. Further, the equation (8) indicates that when the total capacitance of the feedback capacitors Cfb1 and Cfb2 is constant, the increase in the feedback voltage Vamp can be effectively reduced by increasing the ratio of the capacitance of the feedback capacitor Cfb2.

Figure 5A:
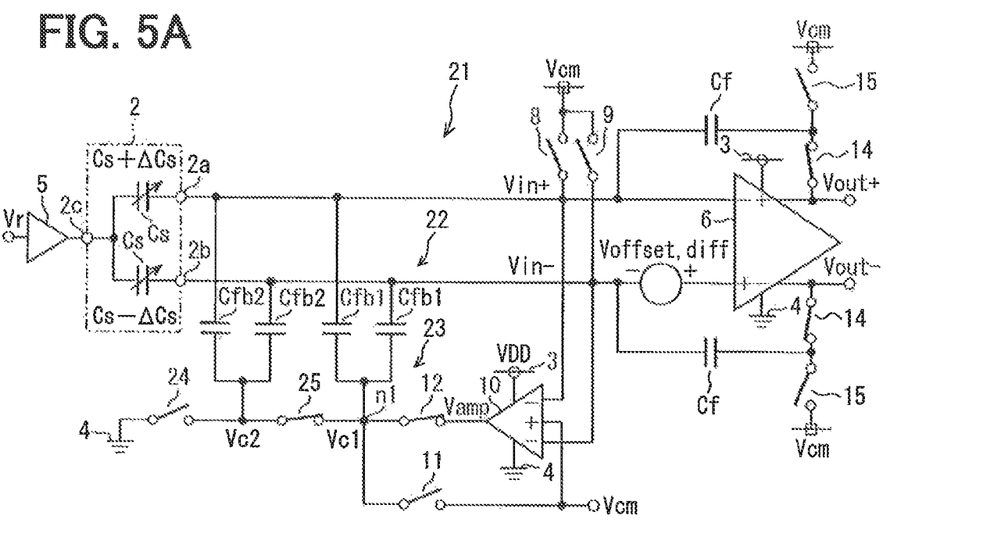
FIG. 5A is a diagram illustrating a structure during the period CV1 and the period CV2 to which an input conversion offset voltage of a sense amplifier is equivalently added.

Next, errors in the offset voltages of the sense amplifier 6 and the feedback amplifier 10 are described. FIG. 5A is a diagram illustrating a structure during the period CV1 and the period CV2 to which an input-referred offset voltage Voffset, diff of the sense amplifier 6 is equivalently added. Input voltages Vin+ and Vin− and output voltages Vout+ and Vout− of the sense amplifier 6 during the period CV1 are given by equations (11), (12), (13), and (14).

$$Vin+ = Vcm + Voffset, diff/2 \quad (11)$$

$$Vin- = Vcm - Voffset, diff/2 \quad (12)$$

$$Vout+ = Vcm + (1 + (Cs + Cfb1 + Cfb2)/Cf) \cdot Voffset, diff/2 \quad (13)$$

$$Vout- = Vcm - (1 + (Cs + Cfb1 + Cfb2)/Cf) \cdot Voffset, diff/2 \quad (14)$$

The input voltages Vin+ and Vin− and the output voltages Vout+ and Vout− of the sense amplifier 6 during the period CV2 are given by equations (15), (16), (17), and (18).

$$Vin+=Vcm+Voffset,diff/2 \quad (15)$$

$$Vin-=Vcm-Voffset,diff/2 \quad (16)$$

$$Vout+=Vcm+2\Delta CsVcm+(1+(Cs+Cfb1+Cfb2)/Cf)\cdot Voffset,diff/2 \quad (17)$$

$$Vout-=Vcm-2\Delta CsVcm-(1+(Cs+Cfb1+Cfb2)/Cf)\cdot Voffset,diff/2 \quad (18)$$

Thus, by calculating the difference between the output voltages Vout+ and Vout− during the period CV1 and the output voltages Vout+ and Vout− held during the period CV2 using the CDS circuit, the physical quantity can be detected without being affected by the input-referred offset voltage Voffset,diff of the sense amplifier 6.

Figure 5B:
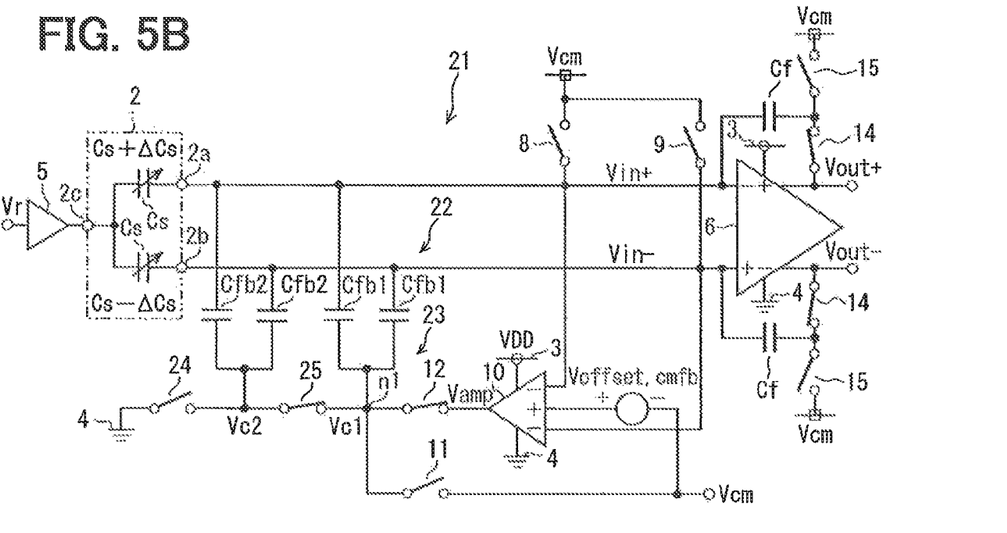
FIG. 5B is a diagram illustrating a structure during the period CV1 and the period CV2 to which an input conversion offset voltage of a feedback amplifier is equivalently added.

FIG. 5B is a diagram illustrating a structure during the period CV1 and the period CV2 to which an input-referred offset voltage Voffset,cmfb of the feedback amplifier 10 is equivalently added. The input voltages Vin+ and Vin− and the output voltages Vout+ and Vout− of the sense amplifier 6 during the period CV1 are given by equations (19), (20), (21), and (22).

$$Vin+=Vcm+Voffset,cmfb \quad (19)$$

$$Vin-=Vcm+Voffset,cmfb \quad (20)$$

$$Vout+=Vcm-\Delta Cs/Cf\cdot Voffset,cmfb \quad (21)$$

$$Vout-=Vcm+\Delta Cs/Cf\cdot Voffset,cmfb \quad (22)$$

The input voltages Vin+ and Vin− and the output voltages Vout+ and Vout− of the sense amplifier 6 during the period CV2 are given by equations (23), (24), (25), and (26).

$$Vin+=Vcm+Voffset,cmfb \quad (23)$$

$$Vin-=Vcm+Voffset,cmfb \quad (24)$$

$$Vout+=Vcm+2\Delta CsVcm-\Delta Cs/Cf\cdot Voffset,cmfb \quad (25)$$

$$Vout-=Vcm-2\Delta CsVcm+\Delta Cs/Cf\cdot Voffset,cmfb \quad (26)$$

Thus, by calculating the difference between the output voltages Vout+ and Vout− during the period CV1 and the output voltages Vout+ and Vout− held during the period CV2 using the CDS circuit, the physical quantity can be detected without being affected by the input conversion offset voltage Voffset,cmfb of the feedback amplifier 10.

As described above, according to the present embodiment, since the feedback capacitor Cfb2 is precharged during the period Reset, the increase in the feedback voltage Vamp during the period CV2 is reduced by the charge. Thus, the total capacitance of the feedback capacitors Cfb1 and Cfb2 necessary to keep the input common-mode voltage at the predetermined voltage Vcm can be reduced, so that the physical quantity can be accurately detected.

Further, since the first and second preset voltages used in the present embodiment are only the predetermined voltage Vcm and 0V, a power supply structure can be simplified compared to the first embodiment. Further, the same effect and advantage as the first embodiment can be obtained.

(Modifications)

While the present disclosure has been described with reference to embodiments thereof, it is to be understood that the disclosure is not limited to the embodiments. The present disclosure is intended to cover various modifications and equivalent arrangements within the spirit and scope of the present disclosure.

In the second embodiment, the first preset voltage applied to the other end of the feedback capacitor Cfb1 during the period Reset and the second preset voltage applied to the other end of the feedback capacitor Cfb2 during the period Reset are not limited to the predetermined voltage Vcm and 0V, respectively, as long as the voltage Vc1 of the node n1 can become equal to the preset voltage Vreset described in the first embodiment when the feedback capacitors Cfb1 and Cfb2 are connected in parallel to each other during the period CV1.

The CDS circuit is not always necessary in each embodiment. If the CDS circuit is not used, the period CV1 is unnecessary. A means for compensating the offset is not limited to the CDS circuit connected to the latter part. Other means, such as offset canceling function added to the sense amplifier 6, can be used. Even when other means are used, it is preferable that the CDS circuit be used in combination.

The same effect can be obtained in each embodiment, even when the first level of the drive signal Vr is 0V, and the second level of the drive signal Vr is 2Vcm. In this case, a voltage direction in which the second level exists relative to the first level with respect to the predetermined voltage means a high voltage direction with respect to the predetermined voltage Vcm. Further, the first level and the second level are not limited to 2Vcm and 0V and can be modified as appropriate to obtain desired detection sensitivity.

What is claimed is:

1. A detection circuit for a capacitive sensor including a pair of sense capacitors with capacitances having a difference responsive to a physical quantity, first ends of the sense capacitors being connected together to provide a common terminal, second ends of the sense capacitors being configured to provide separate detection terminals, the detection circuit comprising:

a drive signal generation circuit capable of generating and applying a drive signal to the common terminal, the drive signal varying between a first level and a second level;

a fully differential sense amplifier having inverting and non-inverting input terminals respectively connected to the detection terminals, the sense amplifier being capable of outputting a differential voltage according to the difference between the capacitances of the sense capacitors; and a common-mode voltage control circuit capable of controlling an input common-mode voltage of the sense amplifier to a predetermined voltage, wherein the common-mode voltage control circuit includes a feedback amplifier, a pair of feedback capacitors, and a voltage switch circuit, the feedback amplifier outputs a feedback voltage according to a difference between the input common-mode voltage and the predetermined voltage, the feedback capacitors have first ends respectively connected to the detection terminals and have second ends connected together, the voltage switch circuit applies a preset voltage to the second ends of the feedback capacitors to charge the feedback capacitors during the first level of the drive signal and applies the feedback voltage instead of the preset voltage to the second ends of the feedback capacitors during the second level of the drive signal, and the preset voltage has a voltage value between the predetermined voltage and a limit voltage outputtable by the feedback amplifier in a voltage direction in which the second level exists relative to the first level.

2. The detection circuit according to claim 1, wherein the voltage switch circuit applies the feedback voltage to the second ends of the feedback capacitors after applying the preset voltage to the second ends of the feedback capacitors during the first level of the drive signal.

3. The detection circuit according to claim 1, wherein capacitances of the feedback capacitors are set so that during the second level of the drive signal, the feedback voltage becomes a voltage value between the predetermined voltage and a limit voltage outputtable by the feedback amplifier in a voltage direction in which the first level exists relative to the second level.

4. The detection circuit according to claim 1, wherein the feedback capacitors include first and second feedback capacitors capable of being connected in parallel, the voltage switch circuit respectively applies first and second preset voltages to the second ends of the first and second feedback capacitors during the first level of the drive signal in such a manner that when the first and second feedback capacitors are connected in parallel, voltages of the second ends of the first and second feedback capacitors become equal to the preset voltage, and the voltage switch circuit applies the feedback voltage to the second ends of the first and second feedback capacitors during the time period where the drive signal is at the second level by connecting the first and second feedback capacitors in parallel.

5. The detection circuit according to claim 4, wherein the first preset voltage is equal to the predetermined voltage, and the second preset voltage is a voltage of a power supply line on a voltage side where the second level exists relative to the first level.

6. The detection circuit according to claim 4, wherein the voltage switch circuit applies the feedback voltage to the second ends of the first and second feedback capacitors by connecting the first and second feedback capacitors in parallel after respectively applying the first and second preset voltages to the second ends of the first and second feedback capacitors during the first level of the drive signal.

* * * * *